US008817264B2

(12) United States Patent
Irani et al.

(10) Patent No.: US 8,817,264 B2
(45) Date of Patent: *Aug. 26, 2014

(54) METHOD AND APPARATUS FOR ANALYZING MULTIPHASE FLUID FLOW USING A MULTIVARIATE OPTICAL ELEMENT CALCULATION DEVICE

(71) Applicant: Halliburton Energy Services, Inc., Houston, TX (US)

(72) Inventors: Cyrus Aspi Irani, Houston, TX (US); Cidar Mansilla Arce, Tomball, TX (US); Hendrik Kool, Conroe, TX (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/870,202

(22) Filed: Apr. 25, 2013

(65) Prior Publication Data
US 2014/0020462 A1 Jan. 23, 2014

Related U.S. Application Data

(63) Continuation of application No. 13/881,128, filed as application No. PCT/US2012/047825 on Jul. 23, 2012, now Pat. No. 8,610,895.

(51) Int. Cl.
*G01N 21/55* (2014.01)
*G01N 33/24* (2006.01)

(52) U.S. Cl.
CPC .............. *G01N 33/241* (2013.01); *G01N 21/55* (2013.01)
USPC .......................................... 356/445

(58) Field of Classification Search
CPC .................................................. G01N 33/2835
USPC ........................................................... 356/445
See application file for complete search history.

(56) References Cited

U.S. PATENT DOCUMENTS

| 5,134,879 | A | 8/1992 | Wong et al. |
| 6,020,960 | A * | 2/2000 | Freud ............................ 356/336 |
| 6,290,576 | B1 * | 9/2001 | Moore et al. .................... 451/41 |
| 7,623,233 | B2 | 11/2009 | Freese et al. |

(Continued)

OTHER PUBLICATIONS

International Search Report for PCT Application No. PCT/US2012/047825 dated Mar. 8, 2013.
Written Opinion for PCT Application No. PCT/US2012/047825 dated Mar. 8, 2013.

*Primary Examiner* — Roy M Punnoose
(74) *Attorney, Agent, or Firm* — Anthony Iannitelli; Booth Albanesi Schroeder, LLC (57) ABSTRACT

A method is presented for analyzing a multiphase fluid flowing through a tubular. A sample fluid flow of multiphase fluid (a mixture of some combination of gas, liquid and solid) is separated from a primary tubular, such as with a probe which traverses the tubular. At least one property of the multiphase fluid is determined using at least one multivariate optical element (MOE) calculating device. Measured properties include the presence, proportional amount, mass or volumetric flow rate, and other data related to a constituent of the fluid, such as $CO_2$, $H_2S$, water, inorganic and organic gases and liquids, or group of constituents of the fluid, such as SARA, C1-C4 hydrocarbons, etc. The multiphase fluid is preferably mixed prior to analysis. Additional data can be gathered and used to calculate derivative information, such as mass and volumetric flow rates of constituents in the tubular, etc.

16 Claims, 7 Drawing Sheets

(56) References Cited

U.S. PATENT DOCUMENTS

| | | | |
|---|---|---|---|
| 7,671,994 B2* | 3/2010 | Shakespeare et al. | 356/432 |
| 7,697,141 B2* | 4/2010 | Jones et al. | 356/445 |
| 8,358,418 B2* | 1/2013 | Myrick et al. | 356/445 |
| 8,610,895 B1* | 12/2013 | Irani et al. | 356/445 |
| 2011/0113899 A1 | 5/2011 | Dahler et al. | |
| 2013/0034842 A1* | 2/2013 | Tunheim et al. | 435/3 |
| 2013/0087723 A1* | 4/2013 | Pelletier et al. | 250/504 R |
| 2013/0155408 A1* | 6/2013 | Irani | 356/445 |

\* cited by examiner

METHOD AND APPARATUS FOR ANALYZING MULTIPHASE FLUID FLOW USING A MULTIVARIATE OPTICAL ELEMENT CALCULATION DEVICE

CROSS-REFERENCE TO RELATED APPLICATIONS

This application is a continuation of U.S. application Ser. No. 13/881,128 filed Apr. 23, 2013 which is a National Stage International Application No. PCT/US2012/047825, filed Jul. 23, 2012. Each patent application identified above is herein incorporated in its entirety by reference for all purposes.

TECHNICAL FIELD

Generally, a method of analyzing multiphase fluid flow (MPF) in a tubular, such as a pipe or wellbore tubular, using a multivariate optical element (MOE) calculation device is provided. More particularly, methods and apparatus are presented for determining the constituent parts of a multiphase flow, for example, a hydrocarbon reservoir fluid, and the quantity and mass flow rate of the constituents utilizing an MOE calculation device.

BACKGROUND

This invention relates to optical analysis systems and methods for analyzing multiphase fluids, for example, reservoir hydrocarbons flowing in a tubular, pipe, or well.

In the petroleum industry, as in many other industries, ability to monitor flow of certain fluids in conduits, tubulars, process pipes and the like, especially in real time, offers considerable value. Oil and gas well operators often need to measure water, oil, gas flow rates, or a combination of these, during production, transportation and processing, and at various locations, such as downhole, at the wellhead, in transport pipelines, etc. Often the fluid is a mixture of multiple phases (oil, gas, water, even solids) and typically consists of many constituents (C1 and higher hydrocarbons, water, asphaltenes, etc.). This information aids in improving well production, making decisions regarding processes to apply to a well, preventing flow problems, and generally determining the well's performance.

While some techniques enable measuring flow rates within two phase mixtures, difficulty arises in determining individual volumetric and mass fractions and flow rates in three phase mixtures. Separators can be used to separate out one or more phases from the flow stream, but they introduce additional equipment and costs and typically require significant space. Other costly and time consuming procedures entail manual sampling of the mixture to obtain information regarding the individual volumetric or mass fractions. On the other hand, flow metering devices can be complex and can restrict flow creating significant pressure loss, such as when venturi based measurements are required, and do not determine the presence or amounts of particular constituents of the fluid.

In many instances, multiphase flow meters utilize a method to measure a flow rate of the entire flow stream and another process to measure volume fractions of oil, water and gas. This measured information, when applied to flow models, enables estimation of each of the individual phase flow rates. However, flow models make assumptions regarding flow characteristics, and do not account for uniqueness of particular fluid flow. In other words, application of flow models with measured total flow and volume fractions does not permit direct measurement of phase velocities and flow rates and does not determine the presence or amount of flow constituents.

Optical spectroscopy is an analytical technique that derives information about the system being evaluated by the interaction of that system with light in the UV to IR range. The interaction changes the properties of the light, specifically the frequency (color), intensity, polarization, or direction (scattering or refraction). Optical spectroscopy is used to analyze samples in an oil field. Optical spectroscopy techniques are costly, slow and cumbersome to implement and frequently require an elevated level of expertise at the well site.

Determining hydrocarbon fluid quality while drilling can impact real-time decisions such as which zones to test among numerous zones in a complex field, and the number and type of samples to take. When fluid samples are acquired, they must be evaluated for contamination, because high levels of contamination can render them useless for future analysis). Petroleum quality information can also affect decisions regarding drilling, logging, production, work-overs, etc. These services require substantial cost and down time. Natural systems, including geological and petroleum systems, rarely are conducive to a classic spectral analysis without extensive sample preparation. Additionally, classical spectroscopy has limited use in determining physical properties and can be costly and cumbersome to implement.

A relatively new technology employs multivariate optical elements (MOE) to analyze fluid flow, such as in petroleum production and pipelines. An MOE is an optical computer that offers advantageous of ruggedness, low cost and accuracy, while also being unobtrusive, and thus is well suited for application to analysis in a petroleum producing field and for petroleum pipeline monitoring in a hostile environment, such as production at elevated underground temperatures and pressures or in remote and hostile settings. MOE computer devices have been used to analyze static fluid samples, with the associated delays of collection, transport and testing. Further, MOE computer devices have been disclosed as useful in analyzing static and moving fluid flows. However, a need exists for improved methods and apparatus to analyze multiphase fluid flow through a tubular to determine constituents and properties of the fluid.

SUMMARY

According to an embodiment of the invention, a method is presented for analyzing a multiphase fluid flowing through a tubular, the multiphase fluid being comprised of a plurality of constituents. A multiphase fluid (a mixture of some combination of gas, liquid and solid) is flowed through a tubular. A sample multiphase fluid flow is separated from the multiphase fluid, such as with a probe assembly which traverses the first tubular. The sample multiphase fluid is flowed through a second tubular and at least one property of the multiphase fluid is determined using at least one multivariate optical element (MOE) calculating device positioned along the second tubular. Properties can include the presence, proportional amount, mass or volumetric flow rate, and other data related to a constituent, such as $CO_2$, $H_2S$, water, inorganic and organic gases and liquids, etc., or group of constituents of the fluid, such as SARA (which is an aggregate analysis of saturates, aromatics, resins, and asphaltenes), C1-C4 and higher hydrocarbons, etc. The method can be performed on a tubular which is part of a pipeline or downhole string, etc. The multiphase fluid is preferably mixed prior to analysis. A probe assembly, such as a movable probe which traverses the tubular, can be used to gather the sample fluid flow. Additional data can be gathered and used to calculate derivative information, such as mass and volumetric flow rates of constituents in the tubular, etc.

BRIEF DESCRIPTION OF THE FIGURES

The features and advantages of certain embodiments will be more readily appreciated when considered in conjunction with the accompanying figures. The figures are not to be construed as limiting any of the preferred embodiments.

DETAILED DESCRIPTION

Well System—Pipeline

Figure 1:
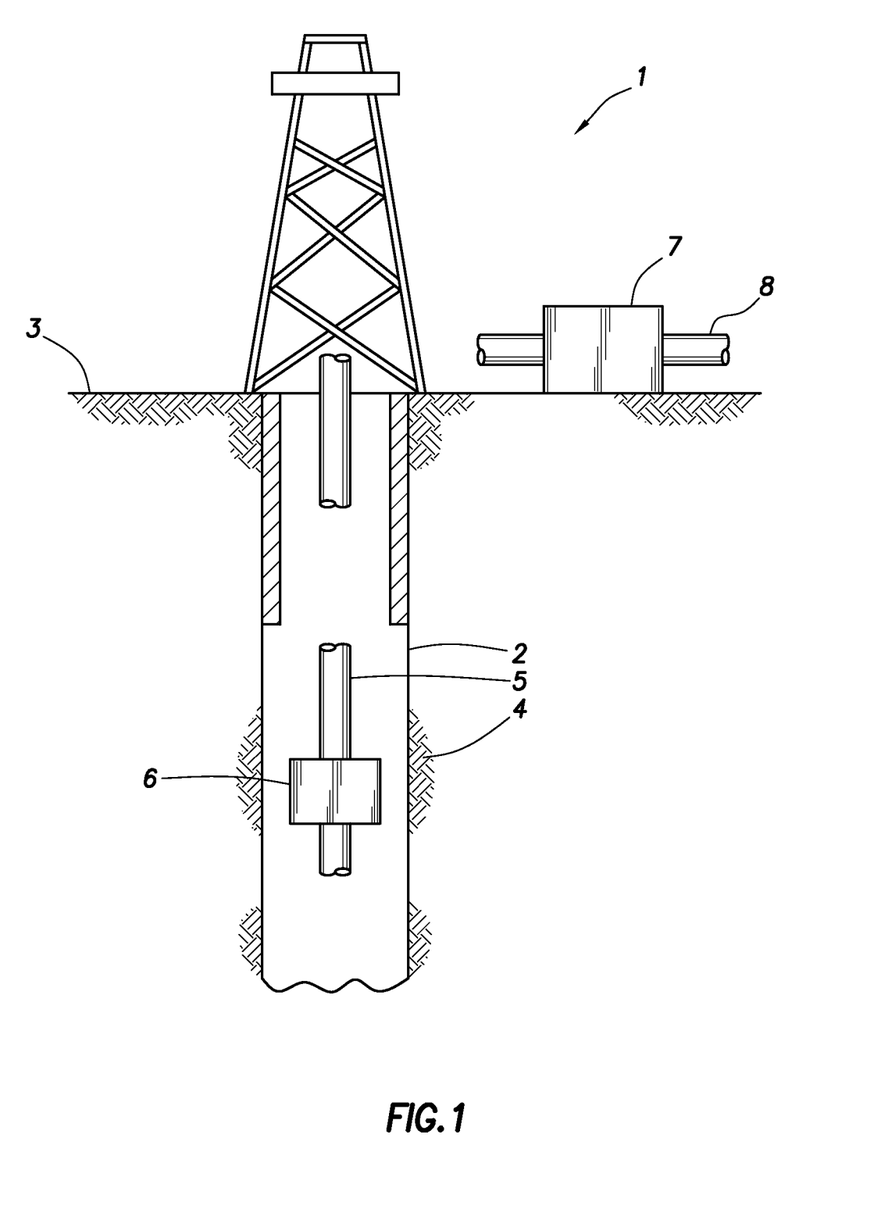
FIG. 1 is a schematic of a well system having MOE calculation devices positioned therein according to an aspect of the invention.

FIG. 1 is a schematic of a well system having MOE calculation devices positioned therein according to an aspect of the invention. An exemplary well 1 has a wellbore 2 extending from the surface 3 into at least one zone 4 of a subterranean formation. An exemplary workstring 5 is shown extending along the wellbore. Exemplary MOE calculating devices 6 and 7 are positioned downhole along the workstring and at the surface along a pipeline 8. The Figure shows exemplary positioning of the MOE calculating devices. The wellbore is seen as vertical but can be deviated or horizontal as well. The wellbore can be cased or uncased. The pipeline 8 can be proximate to or distant from the wellhead, and can be a processing pipeline, a transportation pipeline, having fluid from one or more wells, etc. The workstring is exemplary as well, and can be a drilling string, production string, injection string, test string, or any other type of tubular used in hydrocarbon recovery operations. Further, the MOE calculating device 6 can be positioned at a downhole location along a workstring, wireline or coiled tubing, or positioned along the wellbore independently.

As is evident to those of skill in the art, the MOE calculating device can be used along any tubular where multiphase fluid flow is present or anticipated, whether in conjunction with an oilfield or not. The discussion herein will be made primarily to an exemplary use in analyzing reservoir fluid flowing through a tubular, however, such description is not intended to be limiting.

Tubular

The term "tubular" as used herein means any conduit, tubing, pipe, pipeline, or similar employed to convey multiphase fluid. Tubulars are employed downhole, in pipelines and in processing facilities, for example.

Properties—Groupings

The term "property" means a chemical or physical characteristic or element contained in the multiphase fluid or which forms the multiphase fluid and which includes, but is not limited to SARA (saturates, asphaltene, resins, aromatics), solid particulate content such as dirt, mud, scale, sand, and similar contaminants, water, $H_2O$ ion-composition and content, saturation level, mass readings, hydrocarbon composition and content, gas composition and content, $CO_2$, $H_2S$ and correlated PVT properties including GOR (gas-oil ratio), bubble point, density, a formation factor and viscosity among other properties. Further, the term "property" includes groupings of such elements, compounds, etc., such as, without limitation, C1, C2, C3, C4-C5, C1-C12, and C4-100+ compounds, SARA, solids, etc.>

Further, the term "property" as used herein includes calculated data and information, such as, without limitation, quantities, concentrations, relative proportions and fractions of measured elements and other properties, mass, volume, mass and volume flow rate, etc. of the multiphase fluid and its constituents. Further, the property may be measured indirectly, through measuring an indicator constituent (explained further below).

MOE Calculating Device

The MOE calculating device will be described briefly. For a more complete disclosure of MOE systems and calculating devices, see U.S. Pat. No. 7,697,141 B2, issued on Apr. 13, 2010 to Jones, et al., and U.S. Pat. Nos. 6,198,531 and 6,529, 276 to Myrick, as well as the references cited therein, each of which is hereby incorporated by reference in its entirety for all purposes.

Figure 2:
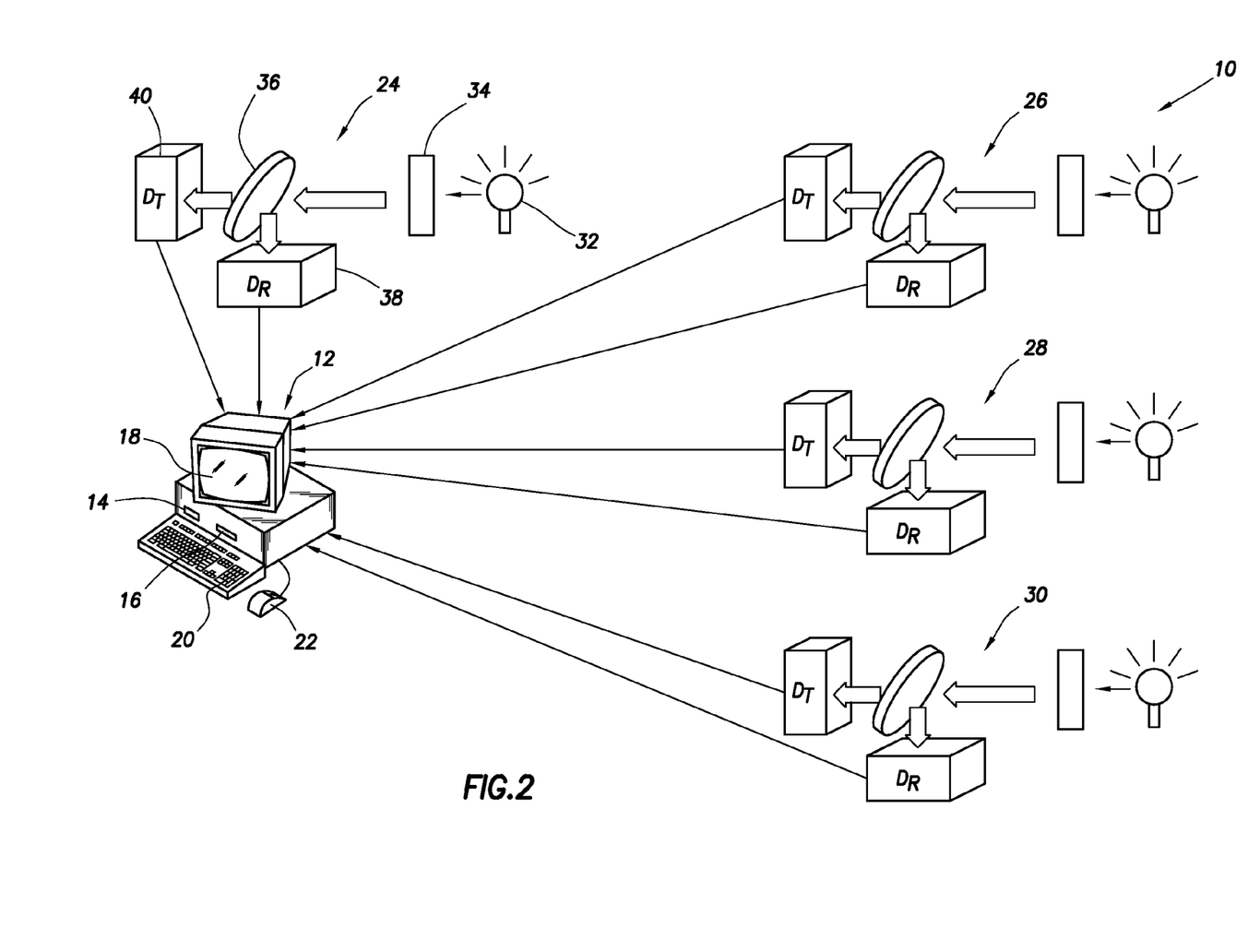
FIG. 2, is a schematic of exemplary MOE calculating devices in a system according to an aspect of the invention.

In FIG. 2, the MOE calculating device 10 is used to determine a plurality of properties of a multiphase fluid flowing through a tubular. System 10 includes apparatuses located at, in contact with (or both) flowing multiphase fluid, which components may be located in a tubular downhole or in a pipeline. The system preferably determines one or more properties of the tested fluid in "real-time."

In FIG. 2, system 10 includes a programmed conventional computer 12 including a microprocessor 14, memory 16 which may include ROM and RAM for storing the analysis program and operating system program and determined data among other information as known in the art of spectral analysis as understood by one of ordinary skill. The computer 12 includes a display 18, a conventional input keypad 20 and a conventional mouse 22. The computer can be located at a location close to, coincident with, or remote from the remainder of the system 10 comprising optical property sensing and optical calculating analyzing devices 24, 26, 28, and 30. While four devices are shown, this number of devices is by way of illustration only, and more or fewer devices may be used in practice. Each device is for detecting and analyzing light interacted with the multiphase fluid and corresponding to a different property of interest. Thus the system 10 may comprise as many calculating devices as there are properties to be determined, each device corresponding to a different property being monitored. The devices are preferably located at or adjacent to a common multiphase fluid flow location.

The optical calculating devices 24, 26, 28 and 30 are rugged, unobtrusive, can withstand the temperatures and pressures in situ at the tubular and thus can be emplaced for long term use. These devices are a marked improvement over present analyzing systems.

The number of four devices is arbitrary and not intended to convey significance. The number of devices in a system depends on the number of tubulars and properties monitored.

The properties of multiphase fluids flowing in different pipes may be monitored by one computer 12, more than one computer 12 may be utilized for multiple multiphase fluid flows in multiple tubulars, and multiple computers may be used to analyze a single multiphase fluid flow. For example, each MOE device can have an associated computer.

Each of the devices 24, 26, 28 and 30 comprises similar elements so that a description of one device 24 is representative. Each device is arranged to determine one property of the multiphase fluid flow. The properties determined include any of those mentioned above, but preferably include at least the presence and quantity of specific inorganic gases such as $CO_2$ and $H_2S$, organic gases such as C1, C2, C3, etc., organic liquids such as aggregates of SARA, water phases and saturation, troublesome solids such as waxes and asphaltenes, etc. As explained herein, detection of properties includes groupings of similar constituents, such as C4-C5, or C1-C6, or saturates, or resins, or aromatics, etc. Other properties, of course, may also be sensed and detected. Further, relationships, ratios and other data is determined by the computer system 12 and based on the data supplied by the various MOE devices, such as, for example, GOR.

Representative device 24 comprises a light source 32, the multiphase fluid 34 being monitored, which should be understood to be flowing as a stream in the tubular and not a static sample, a multivariate optical element (MOE) 36 which is an optical regression calculation device, a detector 38 for detecting light reflected from MOE 36 and a detector 40 for detecting the light transmitted by MOE 36. The MOE is a unique optical calculation device that comprises multiple layers.

Figure 4:
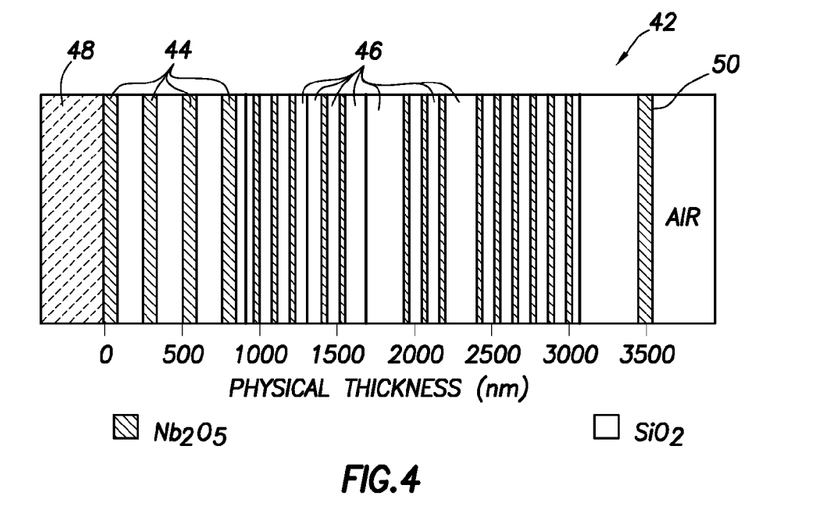
FIG. 4 is a side elevation sectional view of an illustrative representative MOE filter construction.

In FIG. 4, for example, representative optical regression calculating device MOE 42 comprises a plurality of alternating layers 44 and 46 respectively of $Nb_2O_5$ (niobium pentoxide) and $SiO_2$ (quartz). The layers are deposited on a glass substrate 48 which may be of the type referred to in this art as BK-7. The other end layer 50 of the optical calculating layers is exposed to the environment of the installation. The number of layers and the thickness of the layers are determined from and constructed from the spectral attributes determined from a spectroscopic analysis of a property of the fluid flow using a conventional spectroscopic instrument. The combination of layers corresponds to the signature of the property of interest according to the spectral pattern of that property. The spectrum of interest of a given property typically comprises any number of wavelengths. It should be understood that the MOE of FIG. 4 is provided for purposes of illustration only, is not to scale, and bear no correlation to any property to which the invention is directed.

The multiple layers have different refractive indices. By properly selecting the materials of the layers and their spacing, the optical calculation device can be made to selectively pass predetermined fractions of light at different wavelengths. Each wavelength is given a predetermined weighting or loading factor. The thicknesses and spacing of the layers may be determined using a variety of approximation methods from the spectrograph of the property of interest. These methods may include inverse Fourier transform (IFT) of the optical transmission spectrum and structuring the optical calculation device as the physical representation of the IFT. The approximations convert the IFT into a structure based on known materials with constant refractive indices.

The weightings that the MOE 42 layers apply at each wavelength are set to the regression weightings described with respect to a known equation, or data, or spectral signature. The optical calculation device MOE 42 performs the dot product of the input light beam into the optical calculation device and a desired loaded regression vector represented by each layer for each wavelength. The MOE 42 output light intensity is directly related and proportional to the desired property. The output intensity represents the summation of all of the dot products of the passed wavelengths and corresponding vectors.

If the property is the grouping of C4-C5 expected to be found in the multiphase fluid flow, for example, and the regression vectors are that of the C4-C5 grouping, while the intensity of the light output of the MOE is proportional to the amount of C4-C5 grouping in the sample through which the light beam input to the optical calculation device has either passed or has been reflected from or otherwise interacted with. The ensemble of layers corresponds to the signature of the C4-C5 grouping. These wavelengths are weighted proportionately by the construct of the corresponding optical calculation device layers. The resulting layers together produce an optical calculation device MOE 42 output light intensity from the input beam. The output light intensity represents a summation of all of the wavelength's dot products and the loaded vectors of that property. The output optical calculation device intensity value is proportional to the amount of C4-C5 grouping in the multiphase fluid flow being examined. In this way, an MOE optical calculation device is produced for each property to be determined in the multiphase fluid flow.

Figure 5:
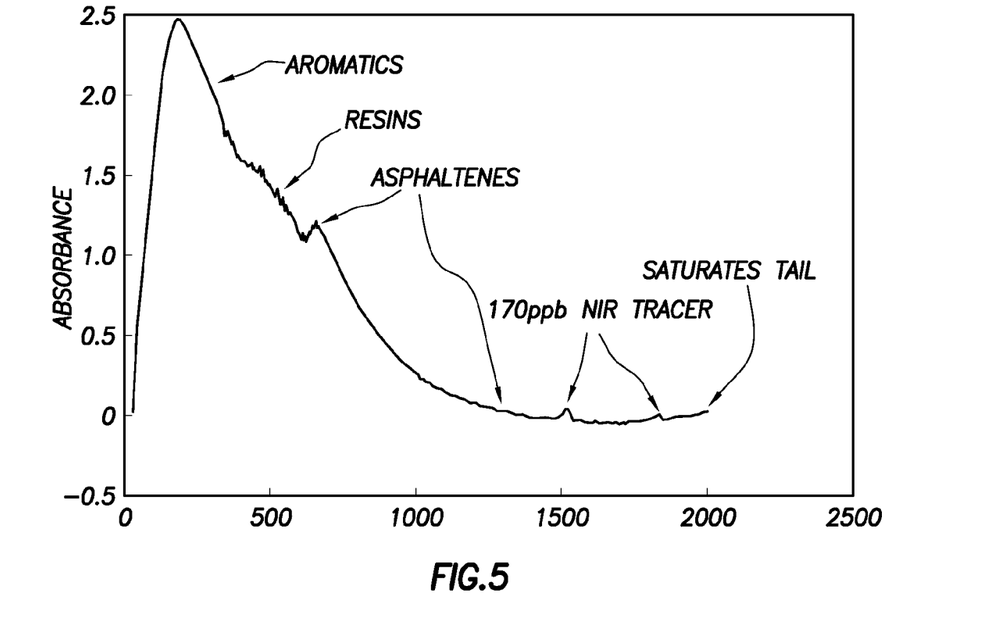
FIG. 5 is a graph of absorbance vs. wavelength representative of crude petroleum broad band spectra illustrating the principle component properties of the crude petroleum.

Such MOE optical calculation devices represent pattern recognition devices which produce characteristic output patterns representing a signature of the spectral elements that define the property of interest. The intensity of the light output is a measure of the proportional amount of the property in the test media being evaluated. For example, in FIG. 5, the broadband spectra of the multiphase fluid flow sample is shown to include aromatics, resins, asphaltenes, and saturates in which absorption is a function of wavelength. A 1270 ppb near infrared tracer (NIR) is shown at about 1500-1800 nm. The saturates are located at the high end of the spectrum.

Not all properties can be correlated to optical interaction. For instance, pH is not specifically optically active. However, a concentration of such physical and chemical properties may induce an optical change in a secondary material, referred to as an indicator. For instance, the addition of methylene blue to an optically inactive water sample allows pH to be optically measured. Many chemical species that are optically inactive in convenient spectroscopic regions can be measured indirectly through the use of an indicator. Coulimetric spectroscopy is the term for this type of spectroscopy. An advantage of multivariate calibrations is that they can be used to mitigate interferences and sample matrix effects. Another advantage of some multivariate calibrations are that the concentrations of the interference or cause of the matrix effect never need be known. To perform a matrix-independent, interference-free calibration, only the independent matrices and independent interferences need to be used. The regression will fail if an un-calibrated component (matrix or interference) appears in a sample.

For further disclosure regarding MOE calculating devices, their use, real time optical computing, etc., see the following, which are each incorporated herein by reference in their entirety for all purposes: U.S. Pat. No. 8,049,881, issued Nov. 1, 2011, entitled Optical analysis System and Methods for Operating Multivariate Optical Elements in a Normal Incidence Orientation; U.S. Pat. No. 8,154,726, issued Nov. 27, 2006, Optical Analysis System and Method for Real Time Multivariate Optical Computing, U.S. Pat. No. 7,623,233, issued Nov. 24, 2009, Optical Analysis Systems and Methods for Dynamic, High-Speed Detection and Real Time Optical Computing.

Representative MOE Set-Ups

Figure 3:
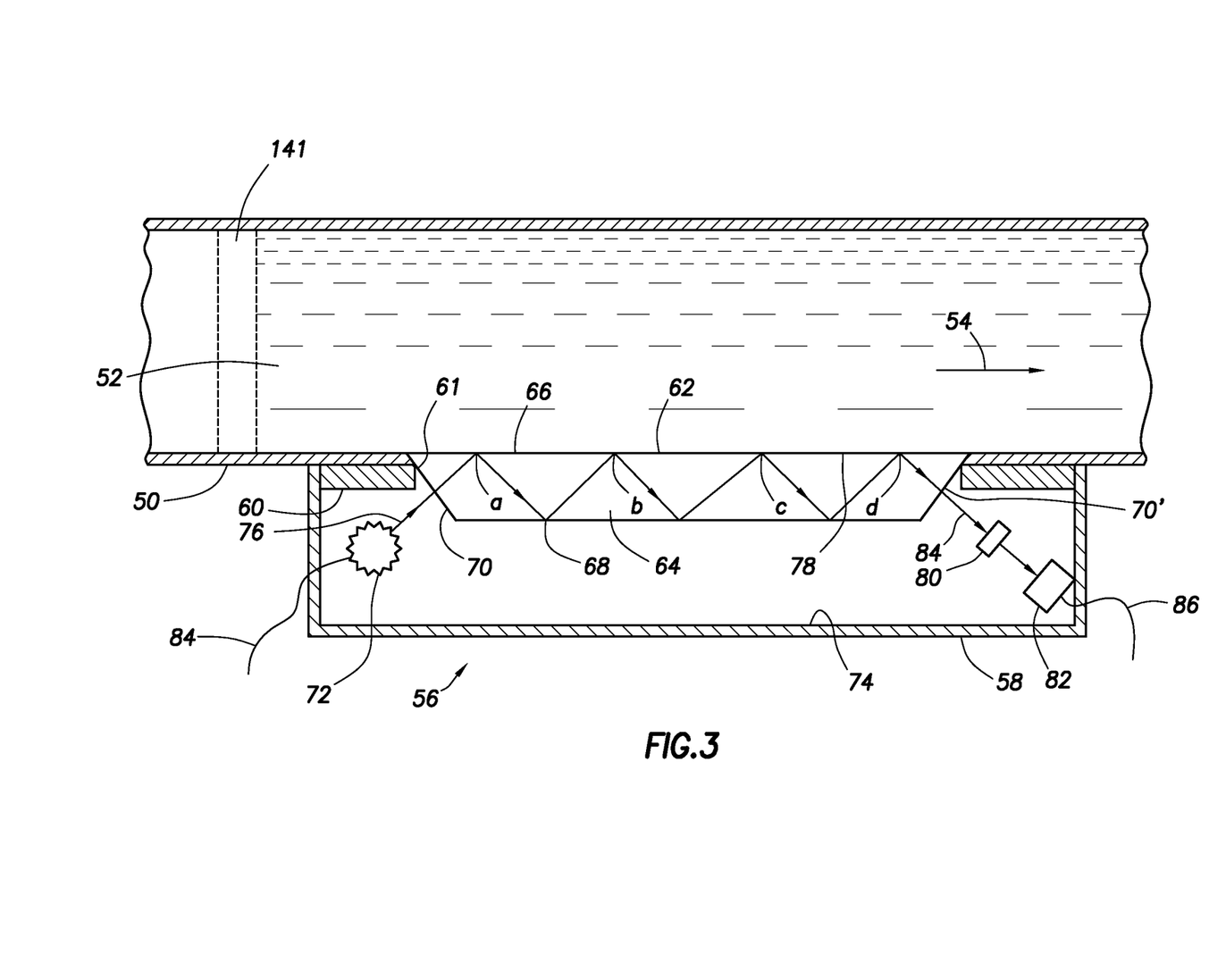
FIG. 3 is a sectional elevation side view of a portion of a tubular illustrating a representation of an embodiment of the invention.

In FIG. 3, a representative tubular 50 may be part of a pipeline, downhole tubular, etc. A multiphase fluid 52 is flowing in the tubular in direction 54. Attached to the tubular 50 is an optical MOE property detecting apparatus 56. Apparatus 56 corresponds to one of the devices 24, 26, 28 and 30 of FIG. 2, and is utilized in a system such as system 10 shown in FIG. 2 for determining properties of the multiphase fluid flowing in the tubular 50. The system utilizing the apparatus 56 determines the amount of the property for which apparatus 56 is attuned in real-time and reports that amount as it occurs in the flowing stream 52. Additional apparatus (not shown) are also provided for detecting and measuring the amounts of additional properties for which they are attuned.

The apparatus 56 comprises a housing 58 and a frame 60, which may be stainless steel, may be magnetized and may have protective coatings. The housing is preferably magnetic so that it is readily attached and detached from the metal pipe 50 but may be attached in other ways. The tubular 50 has an opening 62 forming a window transparent to light, including the IR spectrum.

An internal reflectance element (IRE) 64, which can be an optically transparent disc, prism, or other shape, or a pair of spaced optically transparent plates (not shown), is attached to the frame 60 in the frame opening 61 enclosing and sealing the opening 62. The IRE may be bonded or attached to the frame. The IRE 64 has two spaced parallel planar surfaces 66 and 68 and an outer annular inclined facet 70, defined by the Brewster angle, dependent upon the materials of the interface and wavelength of the light, to the surfaces 66 and 68. A light source 72 is located in the housing cavity 74 and is located to cause its light 76 to be incident on the facet 70 at a right angle thereto. The facet is also at the Brewster angle to the surface 78 of the multiphase fluid 52 flowing in the tubular 50 contiguous with the IRE surface 66. The IRE 64 and frame 60 seal the tubular opening in conjunction with a gasket, etc. (not shown). The attachment of the housing 58 and frame 60 to the tubular 50 is sufficient to withstand anticipated pressures.

Located in the cavity 74 of the housing 58 is a MOE optical calculation device 80 and a detector 82 responsive to the output of the optical calculating device 80 for generating an electrical intensity output signal whose value corresponds to a property of the multiphase fluid being determined. A conductor 84 supplies power to the light source 72 and a conductor 86 receives the detector output signal. The conductor 86 can be connected to a computer 12 (FIG. 2) for determining the property of the fluid manifested by the signal on conductor 86. A transparent fluid (not shown) in the housing cavity 74 may be pressurized to balance the pressure of the petroleum in the pipe 50 to prevent leakages there between. In the alternative to hard wiring the apparatus 56 components, a battery, a local generator or telemetry could also be used to power the apparatus components.

In operation of the apparatus 56, the light 76 from the source 72 is transmitted by the IRE to the surface 78 of the flowing multiphase fluid in the tubular 50. It is known that the light 76 incident on and reflected from the fluid surface will penetrate the surface a few micrometers, e.g., 0.3-5 microns. It is also known that penetration into the fluid must be to at least a depth of about 40 microns for the reflected interacted light from the fluid surface 78 to carry sufficient wavelength information about the measured properties. The total path length requirements change depending upon the component being analyzed, the characteristics of the fluid flow, sample type, presence and amounts of gas-liquid-solid phases, water phases, and so on.

As a result, the light 76 from the source 72 is reflected from the multiphase fluid surface 78 and which penetrates the surface to about 5 micrometers at location a. This reflected light from location a is interacted light and is reflected to the inner surface of surface 68 of the IRE to produce further interacted light. Refraction indices of the IRE 64 cause the interacted light to be reflected from the surface 68 back through the IRE to the fluid surface 78 at location b again penetrating to a depth of about 5 micrometers. This reflection process is repeated at locations c and d and other locations (not shown) until an accumulated depth of about 40 micrometers for all of the interactions is achieved. At the last location d, in this example, the reflected interacted light from the petroleum surface 78 is incident on IRE facet 70 at location 70'. Here the reflected light 84 is normal to the facet of the IRE 68 and passes through the facet 70'.

The light 84 is incident on the MOE 80 and passes through the MOE 80 to detector 82. It should be understood that a second detector (not shown) is also responsive to reflected light from the MOE and supplied to a further conductor (not shown) and thus to the computer.

A separate apparatus 56 is preferably provided for each property to be determined from the multiphase fluid flow. The IRE element 64 may have a thickness of about 1-2 mm and a diameter of about 10-20 mm when fabricated of diamond. Since commercially available IRE elements are available in housings that are threaded to petroleum pipes in the form of a hex head bolt, it is convenient to alter the fabrication of such devices to include a detector and MOE as well as the IRE reflectance element as depicted in FIG. 3. The housing of such a commercially available IRE device is in the form of a hex head bolt with the optical diamond element at the tip of the bolt, remote from the head. The shaft and head are optically transparent to receive reflected interacted light for transmission. It is a simple physical alteration to include the additional components in such a commercially available device and add the necessary electrical conductors for the light and detector currents, etc. The method of use can include steps of determining multiple properties of the multiphase fluid, using one or more multiphase fluids sampled. A separate MOE calculation device is preferably provided for each property to be determined.

In FIG. 3, the dashed region 141 represents one or more turbulence generators. Turbulence generators may comprise plates with through holes of the same or different sizes, constrictions, projections into the fluid flow, radial vanes, one or more vortex devices, etc., as are known in the art.

FIG. 6

Figure 6:
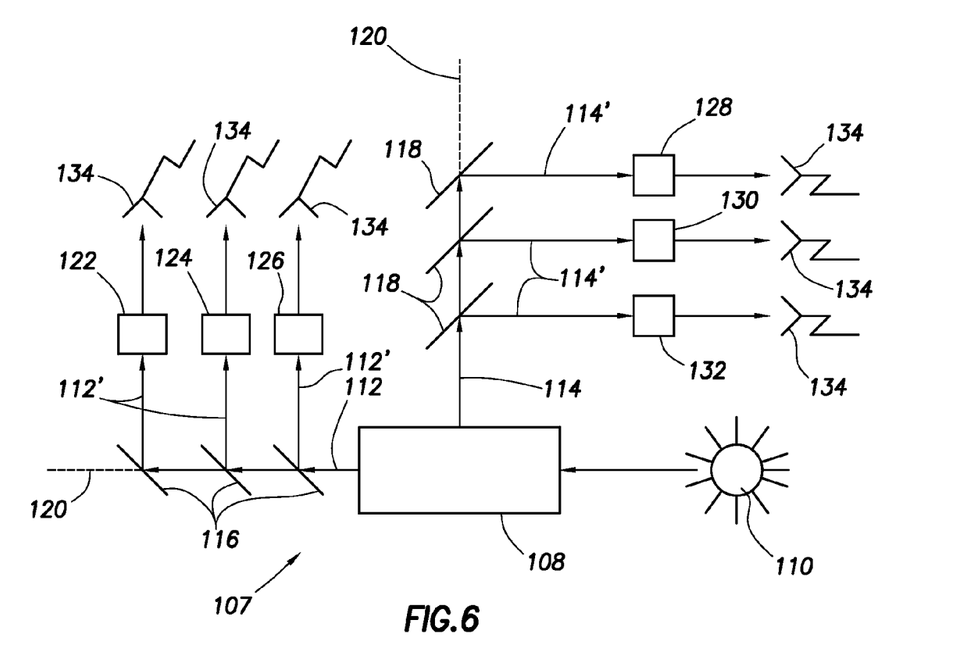
FIG. 6 is a schematic view of an alternative embodiment utilizing a system according to an aspect of the invention.

In FIG. 6, an alternative embodiment is illustrated utilizing a system 107. System 107 comprises a multiphase fluid sample 108. A light source 110 provides light to the sample 108, the light passing through the sample 108. Beam 112 represents absorbed light and beam 114 represents florescence or other emissions. Emissions may occur by applying energy other than light. The IRE relates to light absorption. But, in the case of emissions, different apparatus may be used. Beam 112 is reflected from mirrors 116 and redirected 90 degrees. The mirrors 116 are partially transmissive, forming partially reflected beams 112'. Beam 114 is reflected from partially transmissive mirrors 118, forming partially reflected beams 114'. While three beams 112 and three beams 114 are shown, in practice more (or fewer) than three beams may be utilized as represented by the dashed lines 120. The reflected and transmitted beams are not frequency biased.

The reflected beams 112' are directed to corresponding MOEs 122, 124 and 126. The reflected beams 114' are directed to corresponding MOEs 128, 130 and 132. The output signals of the MOEs are detected by detectors 134 whose outputs are analyzed by a computer (not shown). By way of example, four different spectrums are analyzed by the absorbance MOEs 122-126, and so on, and similarly by the florescence or emission sensitive MOEs 128-130, and so on. This exemplary system thus obtains four (or more) different measurements on four different properties at the same time. The outputs of the detectors 134 associated with beams 112 and 114 results in a property that is proportional to the sum of two MOE detected signals, one from each spectroscopic absorbent and fluorescent component, which represent one property. Thus four different properties are analyzed with both an absorbent and/or a fluorescent (emissive) beam.

Other arrangements than those shown in FIGS. 2 and 6 will be apparent to one skilled in the art. The point here is that light or energy can be transmitted from a single or multiple sources through or reflected from a multiphase fluid sample, at the same or different locations, and one or multiple properties detected from one or more energy or light sources. In a preferred embodiment, multiple properties are detected and measured in a single tubular using MOE(s) and computer(s) located at the same location.

Flow Diagram

Figure 7:
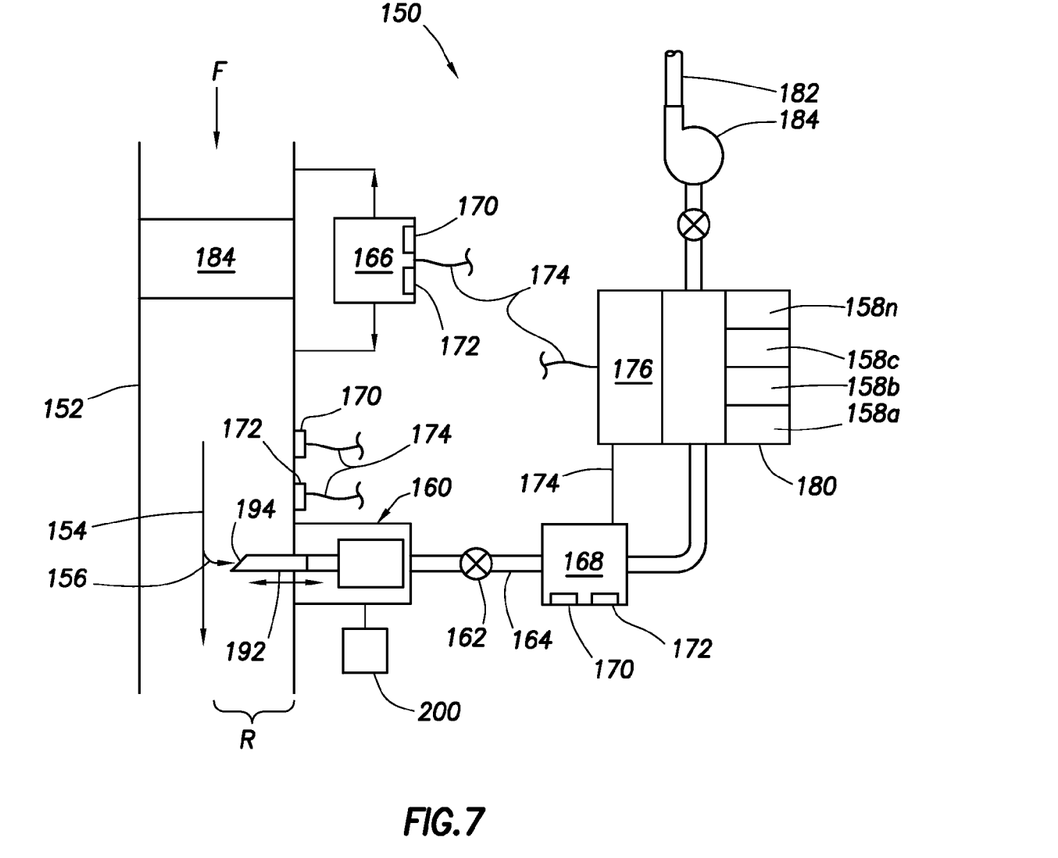
FIG. 7 is a schematic view of an exemplary fluid flow diagram according to an aspect of the invention.

FIG. 7 is a schematic view of an exemplary flow diagram for analyzing a multiphase fluid flow using an MOE calculating device. An exemplary system 150 includes a primary tubular 152 through which a primary stream 154 of multiphase fluid F is flowing. To analyze the fluid, a sample multiphase fluid stream 156 is divided from the primary stream 154 and subjected to at least one MOE calculating device 158 and preferably a plurality of such devices, 158*a*, 158*b*, 158*c* . . . 158*n*. Collection of the sample stream 156 is performed by a sample collection assembly 160, preferably a movable probe assembly, explained in more detail below. The system 150 can also include control valves, such as valve 162, for controlling fluid flow through the various conduits, such as conduit 164. Further, it is anticipated that the system will employ various other fluid characteristic measuring devices, such as a differential pressure fluid meter 166, fluid flow rate (volumetric and/or mass) meter 168, and various pressure sensors 170 and temperature sensors 172, etc. The system 150 also includes a plurality of communication devices for transmitting data, such as wiring 174, wireless devices, etc., as are known in the art. The various data from the sensors, valves, flow meters, and MOE calculating devices are transmitted to a computer 176. Preferably, the computer and MOE calculating devices are located in a single housing 180, although the computer may be remote from the rest of the system.

The system 150 also preferably includes a return conduit 182 for returning the sample fluid either to the primary fluid flow or otherwise disposing thereof. The system can include fluid flow equipment as is known in the art, such as a pump 184, compressors, holding tanks, various valving, such as one-way valves, manual valves, emergency shut-off valves, valve 162, and conduits, such as conduit 164, etc. The use and control of such items is known in the art by persons of skill and will not be discussed herein. Similarly, the differential pressure flow meter 166 and mass or volume flow meter 168 are well known in the art, as are other potential flow meter types, and will not be described in detail herein.

Each MOE calculating device preferably detects and quantifies a target constituent of the multiphase fluid flow in the sample stream. As explained above, the properties to be detected can be the presence and quantities of constituents of the sample multiphase fluid flow, such as inorganic gases, such as $CO_2$ and $H_2S$, organic gases such as C1, C2, C3, etc., organic liquids, such as aggregates of SARA, water phases and saturation, troublesome solids, such as waxes and asphaltenes, and groupings of constituents, such as C4-C5, etc. Further, overall relationships, such as GOR, can be obtained. Operation of MOE calculating devices is explained above herein and in the incorporated references.

Data from the MOE calculating devices is transmitted to the computer 176, or a plurality of computers. Measured data from the various pressure and temperature sensors 170 and 172, and flow meters 166 and 168, and any other data gathering sources. All of this information can then be further manipulated by the computer to derive mass flow rates of the various constituents and components (gas, liquid, solid) of the sample multiphase fluid.

MPF and Mixer

Multiple phase flow is often heterogeneous with segregation along phase densities and viscosities. For example solids sludge to the bottom of a pipe, gas floats to the top, and oil rides on top of water. Lower viscosity fluids tend toward the center of the pipe while higher viscosity fluids tend toward the rim of the pipe. This segregation is often only slight, but nonetheless important to consider. Because petroleum flow is often multiphase flow, it is preferable, for the sake of accuracy, to achieve homogeneous fluid flow in the sample stream before taking measurements, especially when between phases. Separation in flow occurs most often for laminar flow. Therefore, if turbulent flow is introduced in the flowing multiphase fluid upstream of the optical analyzers, then homogeneous sampling will be more probable.

Turbulent flow is best induced over short distances by an obstruction or constriction in the pipe. A constriction in a pipe increases flow rate or velocity and induces turbulent flow. The dimensions of the obstruction depend on the viscosity of the fluids in flow, the diameter of the pipe, and the velocity of the fluid. The dimensions of the obstruction may vary from one application to another, but can be easily designed using commercial design packages such as Stateflow (trademark), a computer program commercially available from Mathworks Company. Other computer programs available are Flowmaster (trademark) from Flowmaster International Limited, State SRL from Fluid Systems Simulation Services and Hydraulic Blockset from Expert Control GmbH.

Preferably, the method of use includes inducing turbulence in the multiphase fluid upstream from the MOE calculating devices to provide homogeneous distribution of different constituents and components receiving reflected light. An exemplary turbulence generator 184 or mixer is seen in FIG. 7 positioned along the primary tubular 152, upstream from the sample collection assembly 160. Alternate locations are possible and multiple turbulence generators may be employed. The turbulence generator may be of any type known in the art, including but not limited to vortex assemblies, such as an in-line vortex mixer, constriction plates, orifices, nozzles, stationary or mobile blades, projections, rotary devices, etc.

Figure 8:
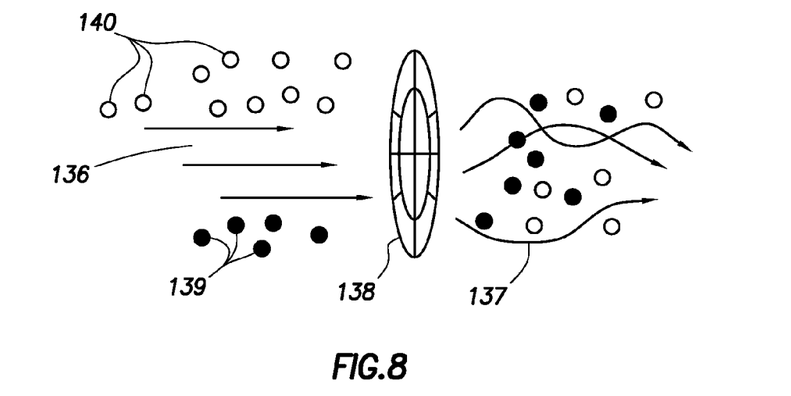
FIG. 8 is a schematic of laminar fluid flow transformed to turbulent flow by a constriction or obstruction in the flow path according to an aspect of the invention.

FIG. 8 shows laminar flow 136 in a pipe transformed to turbulent flow 137 by a constriction or an obstruction 138 in the flow path forming a turbulence generator. The circle dots versus the solid dots represent various phases (e.g., solid dots representing solids, circular dots representing gas).

Probe

Figure 9:
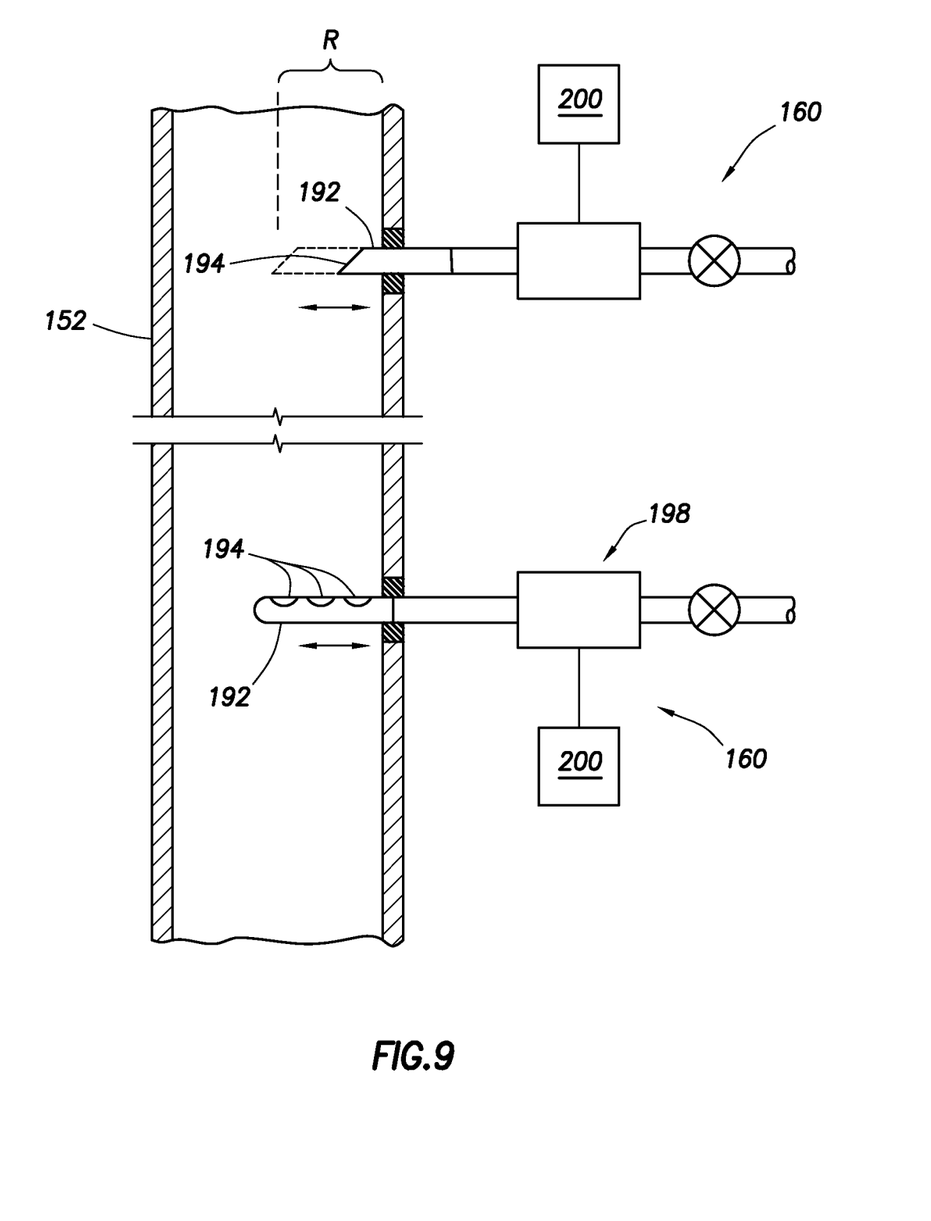
FIG. 9 is a schematic view of an exemplary fluid probe assembly for obtaining a sample fluid flow for analysis according to an aspect of the invention.

FIG. 9 is a schematic view of an exemplary fluid probe assembly 190 for obtaining a sample fluid flow for analysis. By nature of the device, it is not feasible to locate the MOE calculating device into the heart of a large flowing multiphase stream, and even if that was practical, there is still no assurance that the fraction of the flowing stream entering the MOE device is representative of the larger multiphase stream flowing in the primary tubular. Introducing an inline vortex mixer upstream of the detector inlet can assist in making the multiphase mixture more uniform but not necessarily representative at the MOE calculating device. A more accurate sampling strategy is to incorporate both a vortex mixer and a travelling probe such as is used during iso-kinetic sampling. Alternate fluid sampling or flow-dividing systems may be used, as are known in the art, such as static probes, impulse actuated samplers, flow-controlled or time-controlled sampling, impeller type samplers, permanent or removable probes, etc. However, the selected sampling system provides a continuous flow of a sample stream across the MOE calculating devices for continuous analysis. (Of course, the sample fluid flow may be stopped when readings are not desired.)

In the preferred approach, a movable probe 192 which traverses some specific distance, R, usually one radius of the tubular carrying the primary multiphase stream, is introduced into the wall of the pipe. The tip 194 of the hollow probe 192 has a port 194 to collect a sample fluid flow from the primary fluid flow moving past it at any specific moment. By repeatedly traversing the probe across the radial distance and subjecting the collected samples to continuous analysis in the MOE calculating devices, a data stream can be collected, the integration of which should provide an accurate and quantitative description of the various phases flowing through the tubular. The port 194 can be chamfered, angled, etc. Further, the probe can have multiple ports 196, as seen in the alternate embodiment of a probe 198 in FIG. 9. Movement of the probe is preferably powered by an actuator 200, such as a motor, linear actuator, hydraulic or electric power, etc., as is known in the art. Appropriate valving and piping 202 is associated with the probe assemblies.

Support for Method Claims

A method is presented for analyzing a multiphase fluid flowing through a tubular, the multiphase fluid comprised of a plurality of constituents, the method comprising the steps of: flowing a multiphase fluid through a first tubular; separating a sample multiphase fluid flow from the multiphase fluid flowing through the first tubular; flowing the sample multiphase fluid flow through a second tubular; and determining at least one property of the sample multiphase fluid flow using at least one multivariate optical element (MOE) calculating device, the at least one MOE calculating device positioned along the second tubular. The method can further include determining the presence of at least one constituent of the sample multiphase fluid flow; determining the proportion of the at least one constituent of the sample multiphase fluid flow; wherein the proportion is a volumetric or mass proportion; wherein the at least one property includes at least one property selected from the group consisting of: saturates, asphaltene, resins, aromatics, solid particulate, water, $CO_2$, $H_2S$, organic gases, inorganic gases, organic liquids, and inorganic liquids; wherein the at least one property includes a group of constituents of the sample fluid flow; wherein the group of constituents includes at least one of the groups of constituents selected from the group consisting of: C1-C4 hydrocarbons, C1-C8 hydrocarbons, C1-C4 hydrocarbons, C4-C5 hydrocarbons, C4-C100+ hydrocarbons, and SARA; the step of calculating a gas-to-oil ratio, or the mass or volumetric flow rate of the sample multiphase fluid flow; wherein the first tubular is a part of a pipeline or downhole tubular in an hydrocarbon well; the step of mixing the multiphase fluid flowing in the tubular or the sample multiphase fluid flow; wherein the step of mixing is performed using at least one turbulence generator; wherein the turbulence generator is positioned upstream of the at least one MOE calculating device; wherein the step of separating a sample multiphase fluid flow further comprises separating a sample multiphase fluid flow from the first tubular utilizing at least one probe assembly; wherein the at least one probe assembly includes at least one movable probe having at least one port therein for receiving fluid from the multiphase fluid flow in the first tubular; the step of moving the movable probe radially through the first tubular while separating the sample multiphase fluid flow; further comprising measuring pressure, temperature, or flow rate of the multiphase fluid flowing in the first tubular; the step of transmitting data from the at least one MOE calculating device to a computer; wherein the step of determining is done in real time; wherein the multiphase fluid includes gas, liquid and solid constituents; and/or further comprising the step of transmitting data to the computer from at least one sensor or meter positioned along the first tubular.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention. If there is any conflict in the usages of a word or term in this specification and any patent or document incorporated herein by reference, definitions consistent with this specification should be adopted.

What is claimed is:

1. A method of analyzing a multiphase fluid flowing through a tubular, the multiphase fluid comprised of a plurality of constituents, the method comprising the steps of:
   flowing a multiphase fluid through a first tubular;
   separating a sample multiphase fluid flow from the multiphase fluid flowing through the first tubular;
   flowing the sample multiphase fluid flow through a second tubular; and
   determining at least one property of the sample multiphase fluid flow using at least one multivariate optical element (MOE) calculating device, the at least one MOE calculating device positioned along the second tubular.

2. A method as in claim 1, wherein the step of determining further comprises the step of determining the presence of at least one constituent of the sample multiphase fluid flow.

3. A method as in claim 2, wherein the step of determining further comprises the step of determining the proportion of the at least one constituent of the sample multiphase fluid flow.

4. A method as in claim 3, wherein the proportion is a volumetric or mass proportion.

5. A method as in claim 1, wherein the at least one property includes at least one property selected from the group consisting of: saturates, asphaltene, resins, aromatics, solid particulate, water, CO2, H2S, organic gases, inorganic gases, organic liquids, and inorganic liquids.

6. A method as in claim 1, wherein the at least one property includes a group of constituents of the sample fluid flow.

7. A method as in claim 1, wherein the first tubular is a part of a pipeline or downhole tubular in an hydrocarbon well.

8. A method as in claim 1, further comprising the step of mixing the multiphase fluid flowing in the tubular or the sample multiphase fluid flow.

9. A method as in claim 8, wherein the step of mixing is performed using at least one turbulence generator.

10. A method as in claim 9, wherein the turbulence generator is positioned upstream of the at least one MOE calculating device.

11. A method as in claim 1, wherein the step of separating a sample multiphase fluid flow further comprises separating a sample multiphase fluid flow from the first tubular utilizing at least one probe assembly.

12. A method as in claim 11, wherein the at least one probe assembly includes at least one movable probe having at least one port therein for receiving fluid from the multiphase fluid flow in the first tubular.

13. A method as in claim 12, further comprising the step of moving the movable probe radially through the first tubular while separating the sample multiphase fluid flow.

14. A method as in claim 1, further comprising the step of transmitting data from the at least one MOE calculating device to a computer.

15. A method as in claim 1, wherein the step of determining is done in real time.

16. A method as in claim 1, wherein the multiphase fluid includes gas, liquid and solid constituents.

\* \* \* \* \*